United States Patent
Gevins et al.

(10) Patent No.: US 7,551,952 B2
(45) Date of Patent: Jun. 23, 2009

(54) EEG ELECTRODE HEADSET

(75) Inventors: Alan Gevins, San Francisco, CA (US); Robert Howard, Palo Alto, CA (US); Art Sandoval, San Francisco, CA (US)

(73) Assignee: SAM Technology, Inc., San Francisco, CA (US)

( * ) Notice: Subject to any disclaimer, the term of this patent is extended or adjusted under 35 U.S.C. 154(b) by 227 days.

(21) Appl. No.: 11/259,971

(22) Filed: Oct. 26, 2005

(65) Prior Publication Data

US 2007/0093706 A1 Apr. 26, 2007

(51) Int. Cl.
*A61B 5/04* (2006.01)

(52) U.S. Cl. .................. 600/383; 600/393; 600/544

(58) Field of Classification Search .................. 600/383
See application file for complete search history.

(56) References Cited

U.S. PATENT DOCUMENTS

| | | | |
|---|---|---|---|
| 3,490,439 A * | 1/1970 | Rolston | 600/383 |
| 4,537,198 A * | 8/1985 | Corbett | 600/383 |
| 4,632,122 A | 12/1986 | Johansson | |
| 4,683,892 A | 8/1987 | Johansson | |
| 5,357,957 A | 10/1994 | Itil | |
| 5,800,351 A * | 9/1998 | Mann | 600/383 |
| 6,510,340 B1 | 1/2003 | Jordan | |
| 2001/0044573 A1 | 11/2001 | Manolli | |
| 2002/0183605 A1 | 12/2002 | Devlin | |
| 2002/0188216 A1 * | 12/2002 | Kayyali et al. | 600/544 |
| 2004/0073129 A1 | 4/2004 | Caldwell | |

* cited by examiner

*Primary Examiner*—Lee S Cohen
(74) *Attorney, Agent, or Firm*—Eliot Gerber (57) ABSTRACT

An improved electrode headset is provided for the acquisition of electroencephalographic (EEG) brain signals detected at the scalp of a human subject. The headset includes an elastic fabric cap having a chinstrap, which cap is fitted closely to the scalp. The cap has openings at those selected locations on the scalp to which removable and disposable electrodes are to be removably connected to the scalp. A positioning unit, of a generally flat and flexible plastic material, is attachable to the cap by corresponding hook-and-loop fasteners on the outer surface of the cap and the inner surface of the positioning unit. The positioning unit has a base portion and two opposite leg portions, each with slits. Flat beams are adjustably connected through the slits to the leg portions and base portion. Each beam carries a screw member which adjustably applies pressure to electrode holders and a flexible electrode extractor strap to which the electrode holder is attached. Each electrode holder is snap fastened to an electrode positioned within a cap opening.

24 Claims, 7 Drawing Sheets

EEG ELECTRODE HEADSET

GOVERNMENT INTEREST

This invention was made with Government support under contract F41624-99-C-6007 awarded by the Air Force Research Laboratory. The Government has certain rights in the invention.

BACKGROUND OF THE INVENTION

1. Field of the Invention

This invention relates generally to devices for the electroencephalographic (EEG) acquisition of neurophysiological brain electrical signals, and more particularly concerns a headset which is an electrode positioning device. The headset is used for acquiring high quality EEG signals and is comfortable for prolonged usage.

2. Description of Related Art

Functional neuroimaging techniques promise to advance research on neural bases of cognitive processes. There are significant technical differences among the neuroimaging techniques. There are at least four major advantages in using EEG over metabolic imaging techniques (such as PET or fMRI) to study the functions of the human brain. These are: EEG electric field recording reflects actual nerve cell activity (there is no estimated metabolic delay); the brain processes can be followed from millisecond to millisecond (no averaging over seconds and consequent smearing of data); building an EEG laboratory and maintaining it is inexpensive compared to building and running a metabolic imaging laboratory; and, in EEG, delivering stimuli and communication with a subject during recording are relatively uncomplicated.

Scalp recording of brain electrical activity, as ongoing EEG and stimulus-registered Event-Related Potentials (ERPs), has provided useful insights to cognitive functions through neurophysiologic neuropsychology studies employing computerized quantitative analysis of EEG and ERP signals.

For example, advances in detection and analysis of EEG brain neuroelectric signals have allowed EEG monitoring to be useful in assessing neurological disorders, and in laboratory research studies of attention, memory, cognitive ability and the effects of drugs. Devices for monitoring EEG signals for such assessments and studies are typically used in clinics or laboratories or in a home environment, and are typically set up and operated by trained technicians.

In fitting EEG electrodes to the scalp of a subject being monitored, a technician will typically first measure the distances between the nasion and the occipital bone and between the pre-auricular notches-to, identify the top center (Cz) of the head, and will then position all other electrodes relative to these landmarks to comply with the International 10/20 and Extended 10/10 Systems that is generally accepted as the standard for positioning of EEG electrodes. The technician will then part the hair of the scalp of the human subject at the intended electrode sites, clean the sites to remove dirt and hair oil, and gently abrade the scalp to remove the top layer of dead skin to ensure a good conductive connection (low scalp-electrode impedance values).

A number of hats, caps, helmets and headgear are known that have been suggested or developed to position anywhere from 1 to over 120 EEG electrodes according to the International 10/20 and Extended 10/10 Systems. They provide a scalp-electrode interface, with or without the use of an adhesive. However, many of these devices are commonly cumbersome, uncomfortable, and unacceptable for use during prolonged testing periods.

It is desirable to provide an EEG electrode locator headset that utilizes means to accurately identify electrode sites, and gives the technician easy access for application of electrodes to the electrode sites. It is also desirable to provide an EEG electrode headset utilizing a location mechanism allowing a technician to prepare an intended electrode site on the scalp prior to seating and placement of the electrodes.

SUMMARY OF THE INVENTION

The present invention provides for an EEG electrode locator headset that allows the technician to accurately locate and apply disposable EEG electrodes according to the International 10/20 and Extended 10/10 Systems and to allow the acquisition of high quality EEG signals. The EEG electrode locator headset is portable and relatively comfortable, allowing it to be worn by the user during extended testing.

The electrodes in the headset of the present invention are positioned according to the International 10/20 and Extended 10/10 Systems and typically are from five to twenty scalp electrodes. In one preferred embodiment the headset holds seven scalp electrodes. The electrodes are preferably disposable (one-use) electrodes. In addition, in this embodiment the headset supports seven facial electrodes which are connected to the headset.

The headset consists of a flexible elastic fabric cap and a positioning unit (called a "spider"). The positioning unit attaches to the elastic cap with hook and loop fasteners. The positioning unit ("spider") is preferably formed of a flat, flexible and resilient plastic material. The positioning unit normally exerts selected and adjustable inward directed pressure on the electrodes positioned on the subject's head. This pressure on the electrodes, in testing, has provided reliable recording stability.

The U.S. patent literature shows that many types of electrode headsets have been suggested for EEG measurements. In one type of headset a rigid helmet is used with a series of separate air cylinders whose pistons displace the electrodes toward the subject's scalp when contact is desired; see U.S. Pat. No. 4,632,122 to Johansson et al.; U.S. Pat. No. 5,357,957 to Itil et al. and U.S. Pat. No. 4,683,892 to Johansson et al. In U.S. patent application Ser. No. Ser. No. 2002/01882160 to Kayyall et al. electrodes are connected to amplifiers mounted on a rigid headset band. In U.S. patent application Ser. No. 2002/0183605 to Devlin et al. disposable electrodes are fitted over the temple and forehead. U.S. Pat. No. 6,510,340 to Jordan discloses an EEG electrode placement template using straps. U.S. patent application Ser. No. 2004/0073129 to Caldwell et al. discloses a head fixture with sockets for electrodes which are dry or semi-dry. In U.S. patent application Ser. No. 2001/0044573 to Manolli et al. a stretch mesh cap of elastic fabric and elastic straps is used to position electrode locators.

DETAILED DESCRIPTION OF THE INVENTION

Figure 4:
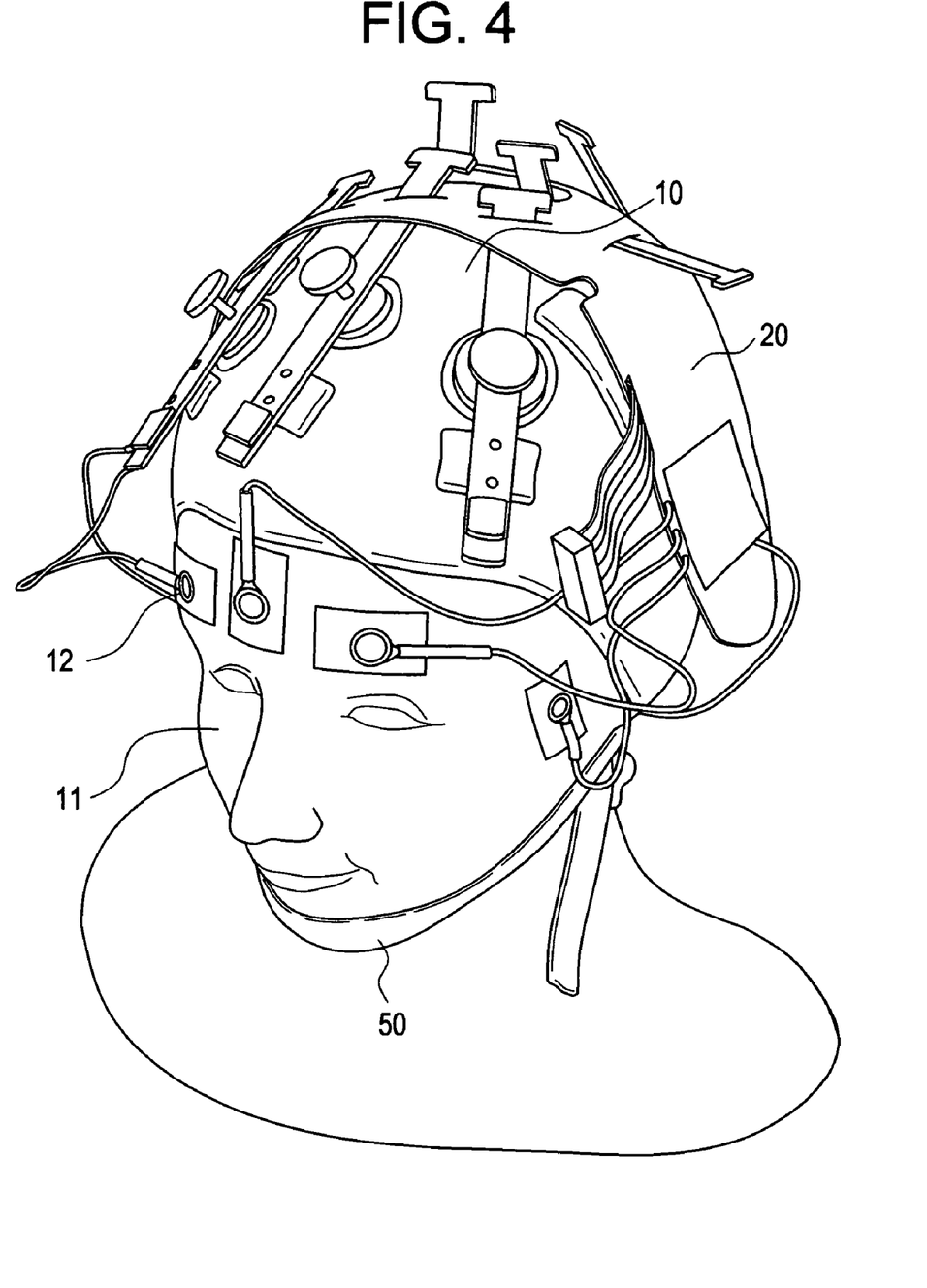
FIG. 4 is a perspective view of the headset of the present invention.
Figure 5:
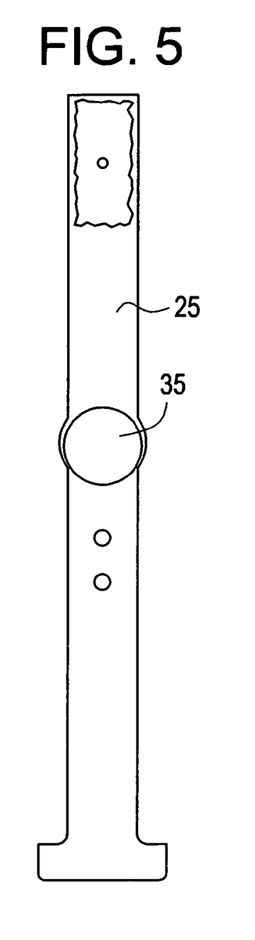
FIG. 5 is a top plan view of one beam of the positioning unit.

As shown in FIG. 4 the elastic fabric cap 10 is placed on the head of the subject 11 and then the positioning unit 20 is placed and fastened on top of the cap 10 with hook and loop fasteners.

Figure 10:
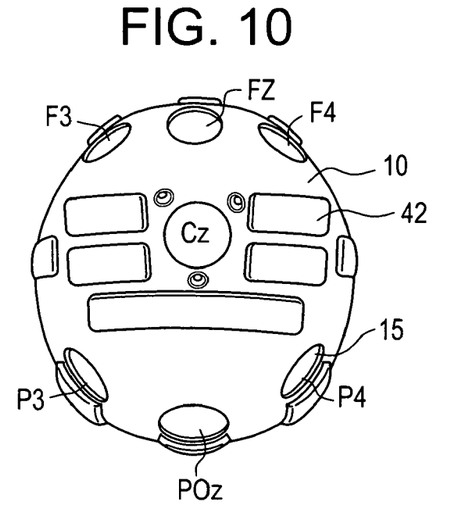
FIG. 10 is a top plan view of the elastic fabric cap.
Figure 11:
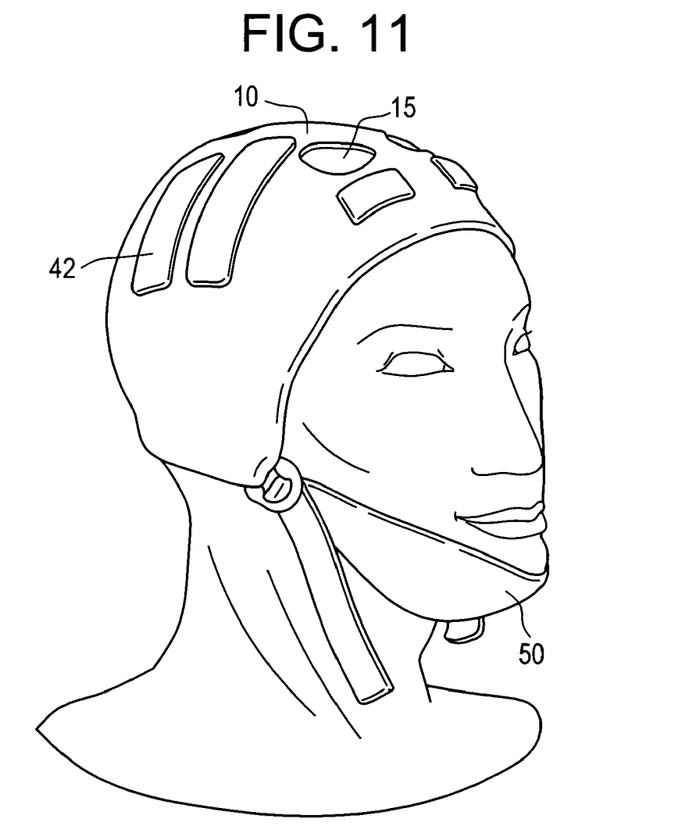
FIG. 11 is a perspective view of the elastic fabric cap with chin strap.

As shown in FIGS. 10 and 11, the cap 10 is an elastic fabric head covering. Preferably the cap 10 is provided in various sizes to fit different head sizes (typically 50-62 cm), for example, three sizes will fit most children and adult women and men. The cap is washable and may be re-used after it has been washed and sterilized.

As shown in FIG. 10, the cap 10 has openings 15 (holes) to locate the positions of the scalp electrodes. These openings 15 provide an accurate placement of the electrodes. In the embodiment of FIG. 10 there are seven openings 15 at the locations, in the International 10/20 and Extended 10/10 Systems, of scalp electrodes F3, F4, Fz, Cz, P3, P4 and POz. In other embodiments, electrodes could be placed at other scalp positions or at a fewer or greater number of sites, depending on the specific requirement of the medical or research application.

The chinstrap 50 is used to help maintain the headset in its correct position. It is preferably an elastic fabric strap which is placed under the chin of the subject. It may be adjusted, using rings or other hardware, to be comfortable and yet reasonably tight.

In this embodiment, the elastic cap is provided in three sizes, which are small (50-54 cm head circumference); medium (54-58 cm head circumference); and large (58-62 cm head circumference). The subject's head is measured and the correct size of cap is placed on the subject's head. The elasticity of the fabric cap enables the holes to maintain the positions of the proportional spacing of the electrodes on all heads within the size range of the cap.

The scalp electrodes are preferably disposable (single-use) solid gel bioelectric monitoring electrodes whose face is sticky and covered with a removable sheet.

Preferably the electrode headset uses self-stick electrodes with hydrogel pellets and metal snap connectors for the facial 12 placement positions and hydrogel electrodes with metal snap connectors for the scalp 23 and 25-30 placement positions. The facial electrodes are each about 15×30 cm including the adhesive area. The scalp electrodes are disks about 2 cm in diameter.

There are seven preferred facial electrode positions in the current embodiment, including ground (center of forehead); Fp2 (directly above the right eye); Fp1 (directly above the left eye); F9 and F10 (outside of the eye and between upper and lower eyelids); and MA1 and MA2 (reference electrodes behind left and right ears respectively).

It is important that the cap be correctly located on the subject so that the electrodes are correctly positioned on the subject's scalp. This may be accomplished by using the Cz position as a reference. The Cz position on the subject's scalp is first located and marked, for example using a grease pencil, after separation of hair at the Cz position. The Cz position is determined using a flexible measuring tape from skull landmarks. Preferably the skull landmark distances are (a) nasion (most indented point on the bridge of the nose) to inion (bony protuberance at the base of the skull) and (b) left to right preauricular notch (protuberance just outside of the left and right ear canals).

The positioning unit ("spider") 20 is used to press the electrodes toward the scalp of the subject in order to obtain good and constant electrode contact with the scalp at the correct selected electrode positions.

Preferably the positioning unit 20 is made of a suitable plastic, which is flexible and elastic and which springs back to its original position. The positioning unit 20 is placed on top of the fabric cap 10 after the cap has been correctly located on the scalp of the subject. The positioning unit 20 is removably attached to the cap with matching hook-and-loop fabric ("Velcro"™) strips 42 on the underside of positioning member 20 and the outer surface of the cap 10. These strips 42 are preferably rectangular as shown in the drawings.

Figure 1:
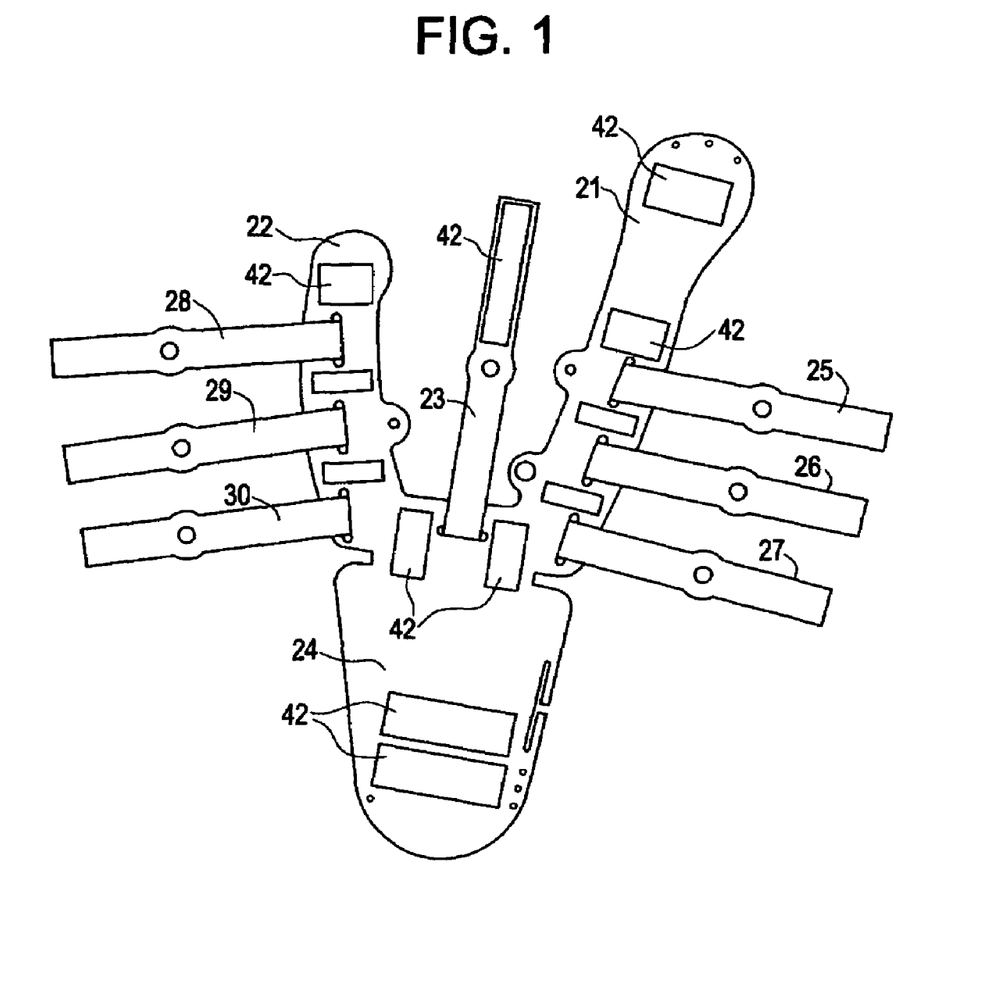
FIG. 1 is a bottom plan view of the underside of the positioning unit, shown without its electrode holders and leads.
Figure 2:
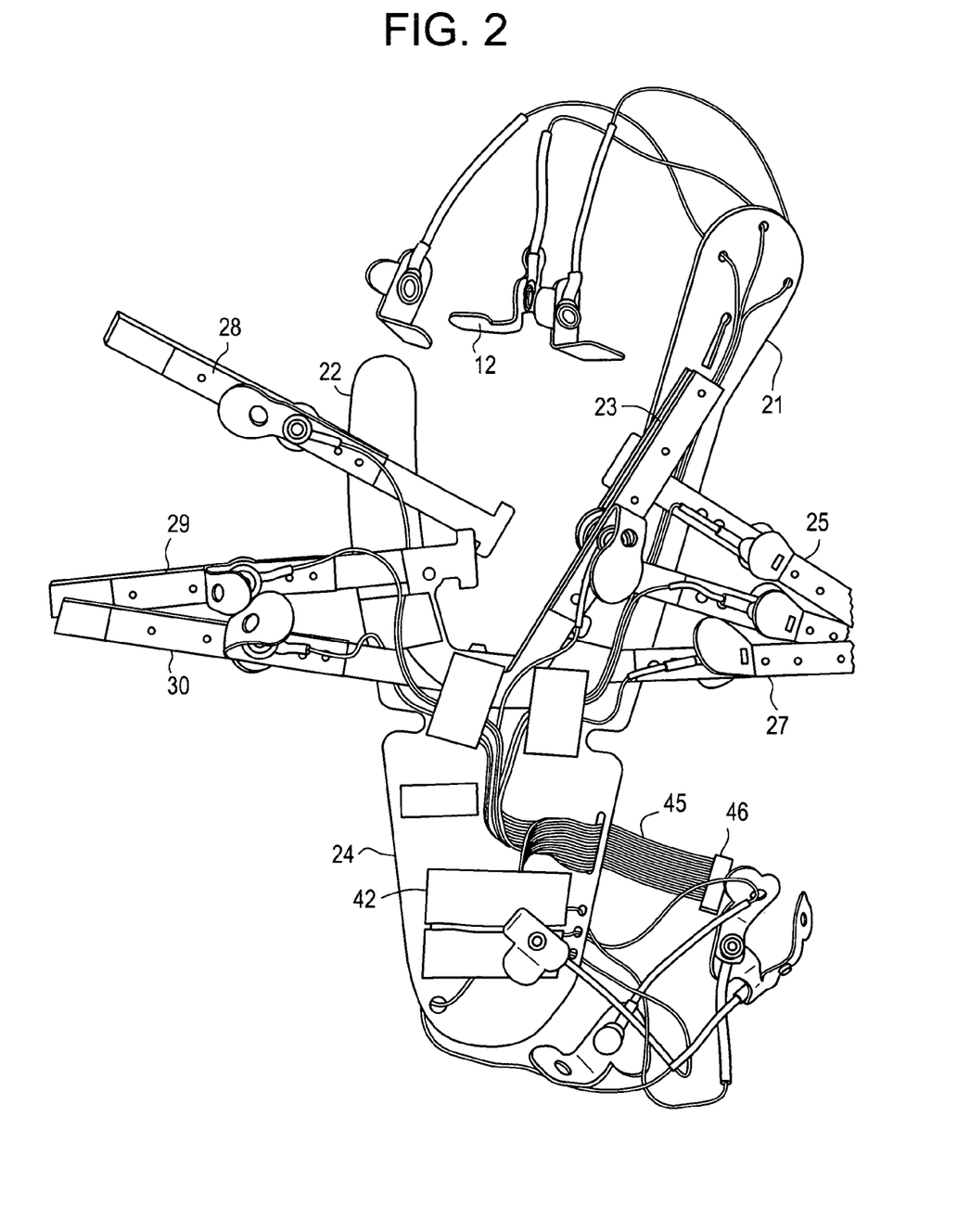
FIG. 2 is a bottom plan view, similar to FIG. 1, but showing the electrode holders and leads.
Figure 3:
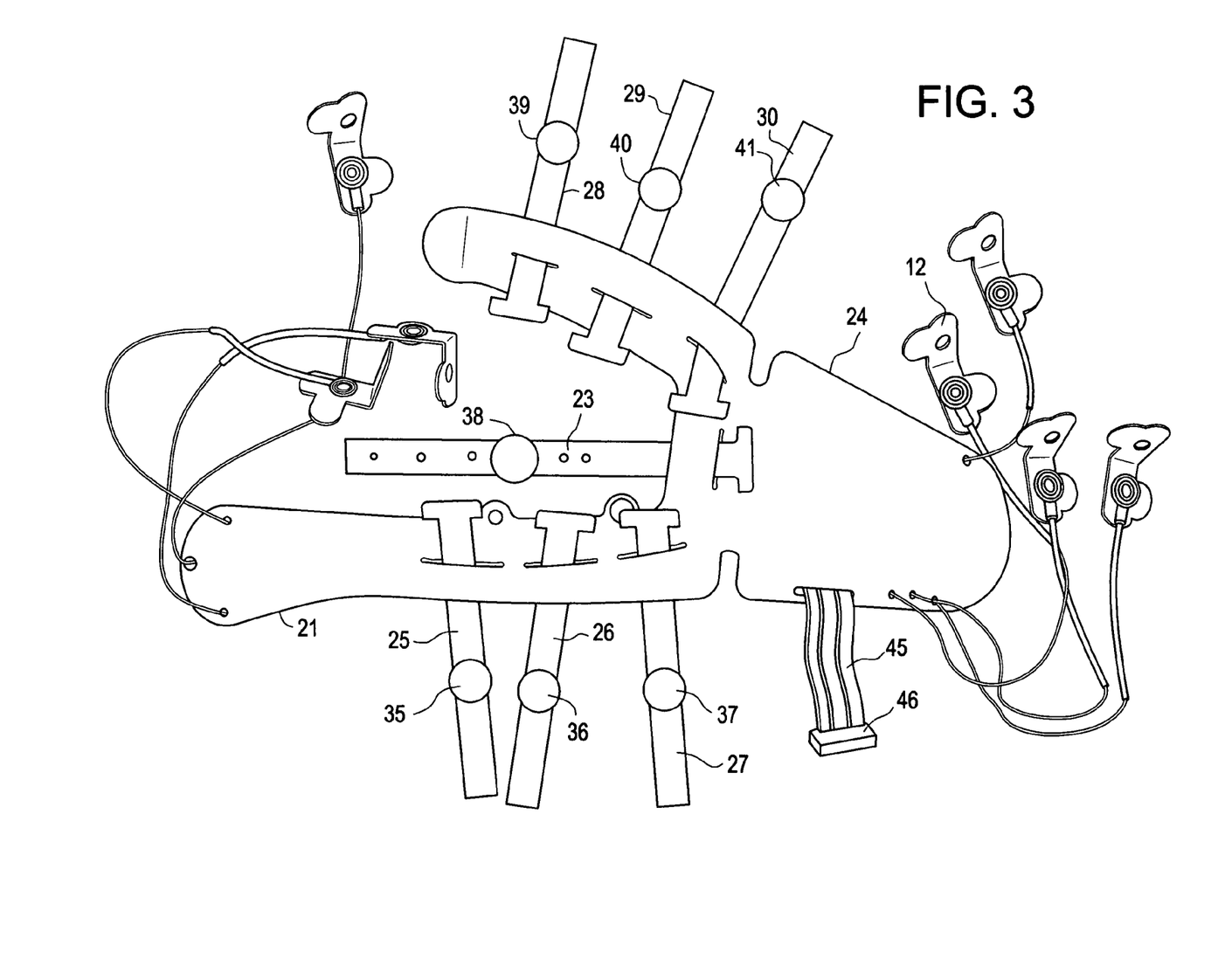
FIG. 3 is a plan view of the top side of the positioning unit and shows the electrode holders and leads.
Figure 9:
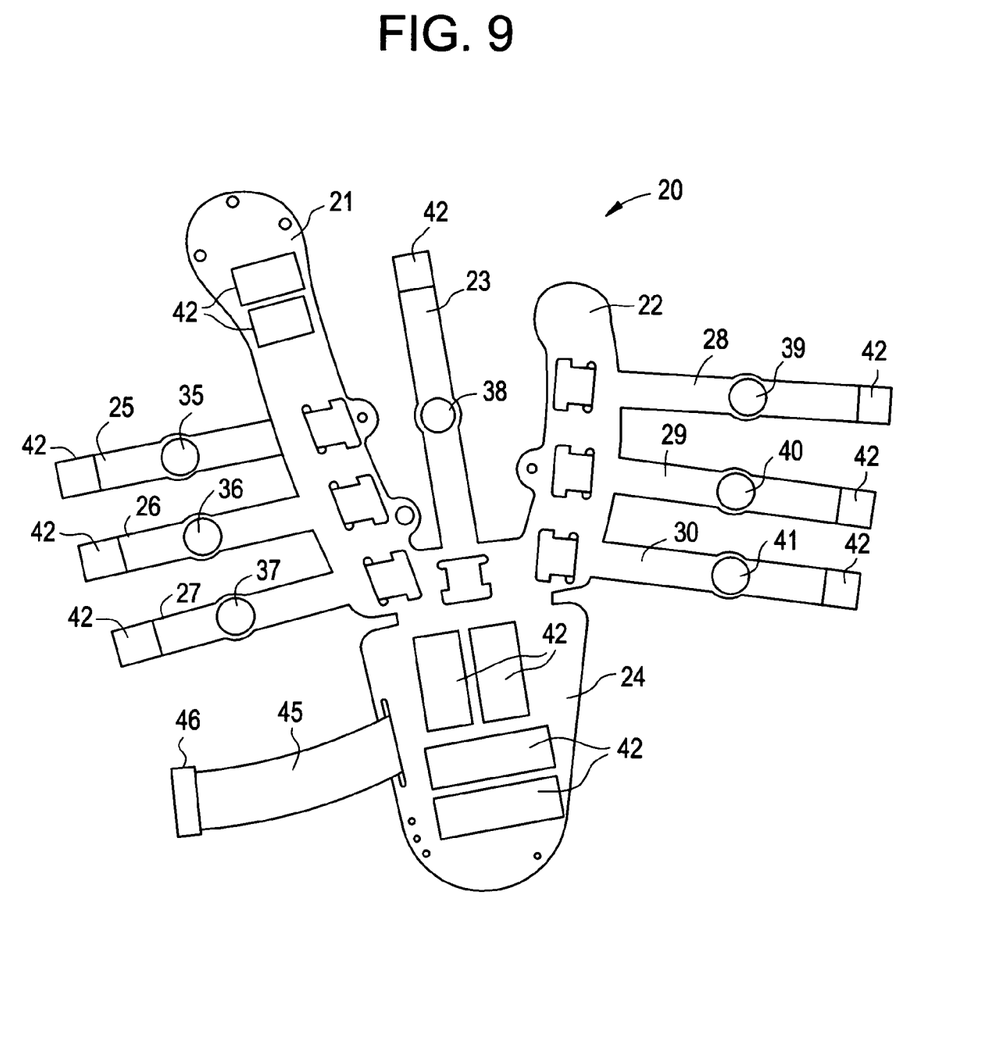
FIG. 9 is a top plan view of the positioning unit.

As shown in FIGS. 1 and 9, the positioning unit ("spider") has two opposite leg portions 21 and 22, a central beam 23 and a base portion 24. The base portion 24 would normally be proximate to the subject's left ear; the beams 25-27 at the front of the subject's head; the beams 28-30 toward the rear of the head and beam 23 toward the subject's right ear.

Each of the leg portions carries 3 extension beams which are front beams 25, 26, 27 (leg portion 21) and rear beams 28, 29, 30 (leg portion 22). The front leg portion 21 and the base portion 24 also carry the facial electrodes which are on free hanging leads.

Figures 6, 7:
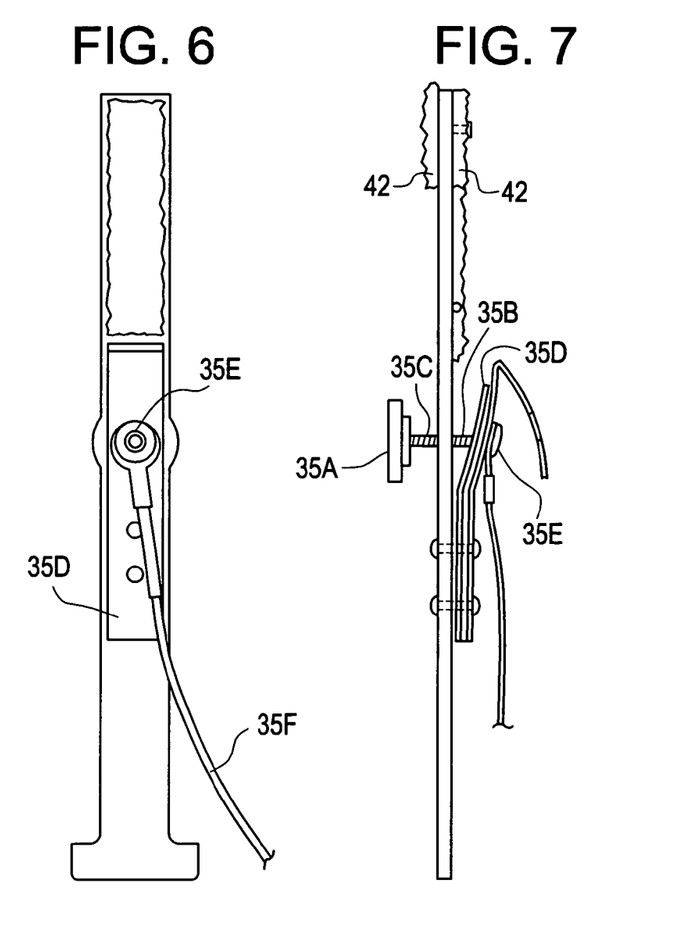
FIG. 6 is a bottom plan view of the beam of FIG. 5.
FIG. 7 is a side plan view of the beam of FIG. 5.
Figure 8:
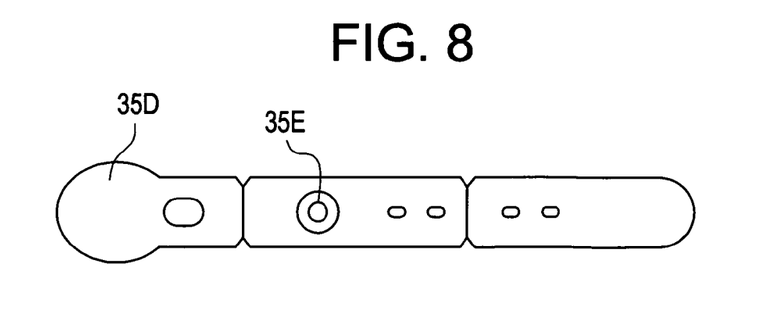
FIG. 8 is a bottom plan view of an electrode extraction strap which is laid flat.

FIGS. 5-8 show views of one of the beams 25, the other beams being similar. Each beam 23 and 25-30 has, near its center, a screw threaded hole and an adjusting member, preferably a screw 35. The outer end of screw 35 is a head 35A which is turnable to adjust the pressure of a scalp electrode on the scalp. The inner end 35B of shaft 35C pushes against a plastic strap 35D which carries an electrode holder 35E. The holder 35E is preferably is a metal snap fastener. The holder 35E is electrically connected to electrode lead (wire) 35F. In FIGS. 6 and 7 the electrode extractor strap 35D is shown in its normal position and in FIG. 8 it is shown in a flat position, prior to folding and installation. The various electrode leads are gathered to form a flat multicolored electrode cable 45 having, at its end, a 14 pin connector 46 (FIG. 9). The connector 46 connects with a connector of an amplifier which is mounted on the base 24 of the positioning unit. Preferably the amplifier is "tinyamps"(™of Sam Technology of San Francisco, Calif.) which is a battery powered multi-channel digital amplifier.

What is claimed is:

1. An electrode headset adapted to fit on the head of a human subject and to carry a plurality of electrodes which removably contacts the scalp of the subject, the headset comprising: A. a cap adapted to fit closely over the scalp, the cap having an inner and an outer surface, a plurality of openings in the cap, each opening being located directly above a selected area of the scalp to which an electrode is adapted to be removably contacted, a plurality of fastening members on the outer surface of the cap; B. a positioning unit adapted to adjustably apply pressure to the electrodes in order to provide their good electrical contact with the scalp, the positioning unit having a body portion and beams both composed of a flexible material, the beams being adjustably attached to the body portion, the body portion having an inner surface and an outer surface, a plurality of fastening members on said body portion inner surface which are adapted to be removably joined to corresponding fastening members on the outer surface of the cap; C. a plurality of pressure adjusting members, each adjusting member being mounted on one of said beams; and D. a plurality of electrode holders, each electrode holder being mounted on one of said beams and to be positioned within one of said cap openings, wherein each adjusting member is in contact with an electrode holder to adjust said holder in relationship to the scalp to vary the pressure of the electrode to the scalp.

2. An electrode headset as in claim 1 wherein the cap is of an elastic fabric.

3. An electrode headset as in claim 2 and including a chinstrap connected to the cap, the chinstrap being adjustable to attach the cap closely to the scalp.

4. An electrode headset as in claim 1 wherein the fastening members are fabric hook-and-loop fasteners.

5. An electrode headset as in claim 1 wherein the body portion is flat and has a base portion and at least first and second leg portions; the headset including a flat central beam adjustably attached to said base portion, at least two flat front beams adjustably attached to the first leg portion, and at least two flat rear beams adjustably attached to the second leg portion.

6. An electrode headset as in claim 5 comprising three beams adjustably attached to the first leg portion and three beams adjustably attached to the second leg portion.

7. An electrode headset as in claim 5 wherein the leg portions and base portion have slits therein and wherein the beams are adjustably attached within said slits.

8. An electrode headset as in claim 1 wherein each electrode holder is attached to a flexible electrode extractor strap, which strap is connected to a beam.

9. An electrode headset as in claim 1 wherein each adjusting member comprises an adjusting screw, having a shaft with a turnable head thereon, and a screw-threaded hole within which the shaft rotates; and the shaft has an end portion which applies pressure to an electrode holder, which pressure is adjustable by rotation of the head.

10. An electrode headset as in claim 1 wherein each electrode holder comprises a metal snap fastener member.

11. An electrode headset as in claim 1 and a wire electrode lead connected to each electrode holder.

12. An electrode headset as in claim 11 and a flat cable composed of a plurality of said wire electrode leads in contact with each other.

13. An electrode headset adapted to fit on the head of a human subject and to carry a plurality of electrodes which contact the scalp of the subject, the headset comprising: A. a plurality of electrodes adapted to removably contact said scalp; B. a cap adapted to fit closely over the scalp, the cap having an inner and an outer surface, a plurality of openings in the cap, each opening being located directly above a selected area of the scalp to which one of said electrodes is adapted to be removably contacted, a plurality of fastening members on the outer surface of the cap; C. a positioning unit adapted to adjustably apply pressure to the electrodes in order to provide their good electrical contact with the scalp, the positioning unit having a body portion and beams both composed of a flexible material, the beams being adjustably attached to the body portion, the body portion having an inner surface and an outer surface, a plurality of fastening members on said body portion inner surface which are adapted to be removably joined to corresponding fastening members on the outer surface of the cap; D. a plurality of pressure adjusting members, each adjusting member being mounted on one of said beams; and E. a plurality of electrode holders, each electrode holder holding at least one of said electrodes and being mounted on one of said beams and within one of said cap openings, wherein each adjusting member is in contact with an electrode holder to adjust said holder in relationship to the scalp.

14. An electrode headset as in claim 13 wherein the cap is of an elastic fabric.

15. An electrode headset as in claim 14 and including a chinstrap connected to the cap, the chinstrap being adjustable to attach the cap closely to the scalp.

16. An electrode headset as in claim 13 wherein the fastening members are fabric hook-and-loop fasteners.

17. An electrode headset as in claim 13 wherein the body portion is flat and has a base portion and at least first and second leg portions; the headset including a flat central beam adjustably attached to said base portion, at least two flat front beams adjustably attached to the first leg portion, and at least two flat rear beams adjustably attached to the second leg portion.

18. An electrode headset as in claim 17 comprising three beams adjustably attached to the first leg portion and three beams adjustably attached to the second leg portion.

19. An electrode headset as in claim 17 wherein the leg portions and base portion have slits therein and wherein the beams are adjustably attached within said slits.

20. An electrode headset as in claim 13 wherein each electrode holder is attached to a flexible strap, which strap is connected to a beam.

21. An electrode headset as in claim 13 wherein each adjusting member comprises an adjusting screw, having a shaft with a turnable head thereon, and a screw-threaded hole within which the shaft rotates; and the shaft has an end portion which applies pressure to an electrode holder, which pressure is adjustable by rotation of the turnable head.

22. An electrode headset as in claim 13 wherein each electrode holder comprises a metal snap fastener member.

23. An electrode headset as in claim 13 and a wire electrode lead connected to each electrode holder.

24. An electrode headset as in claim 23 and a flat cable composed of leads in contact with other leads.

* * * * *